US008149096B2

(12) United States Patent
Metry et al.

(10) Patent No.: US 8,149,096 B2
(45) Date of Patent: Apr. 3, 2012

(54) MEDICATION CONTAINER AND DOSING MONITOR

(75) Inventors: Jean-Michel Metry, Sion (CH); Pierre-Alain Gaillard, Sion (CH); John Urquhart, Palo Alto, CA (US); Bernard Vrijens, Eben-Emael (BE)

(73) Assignee: Aardex Group, Ltd., Sion (CH)

( * ) Notice: Subject to any disclaimer, the term of this patent is extended or adjusted under 35 U.S.C. 154(b) by 0 days.

(21) Appl. No.: 13/134,990

(22) Filed: Jun. 22, 2011

(65) Prior Publication Data

US 2011/0253586 A1  Oct. 20, 2011

Related U.S. Application Data

(63) Continuation of application No. 11/941,796, filed on Nov. 16, 2007.

(60) Provisional application No. 60/859,806, filed on Nov. 17, 2006.

(51) Int. Cl.
*G08B 1/00* (2006.01)

(52) U.S. Cl. ........... 340/309.16; 340/286.01; 340/309.7; 340/539.11; 340/539.12; 340/573.1; 215/228; 221/1; 221/2; 221/3; 221/7; 221/8; 221/9; 221/15; 368/10; 368/28; 368/72; 368/89; 368/107; 368/251

(58) Field of Classification Search ................... None
See application file for complete search history.

(56) References Cited

U.S. PATENT DOCUMENTS

| | | | | |
|---|---|---|---|---|
| 4,588,303 | A | * | 5/1986 | Wirtschafter et al. .......... 368/10 |
| 4,823,982 | A | * | 4/1989 | Aten et al. ........................ 221/3 |
| 5,646,912 | A | * | 7/1997 | Cousin ............................. 368/10 |
| 6,249,717 | B1 | * | 6/2001 | Nicholson et al. ............. 700/241 |
| 2001/0009398 | A1 | * | 7/2001 | Sekura et al. ............... 340/573.1 |
| 2002/0104848 | A1 | * | 8/2002 | Burrows et al. ................... 221/1 |
| 2005/0168337 | A1 | * | 8/2005 | Mahoney ................. 340/539.12 |
| 2006/0139150 | A1 | * | 6/2006 | Brue ........................ 340/309.16 |

\* cited by examiner

*Primary Examiner* — Benjamin C Lee
*Assistant Examiner* — Curtis King
(74) *Attorney, Agent, or Firm* — E. Thomas Wheelock

(57) ABSTRACT

A patient-portable medication event monitor is disclosed which is capable of detecting the dispensing of doses of a particular medication from the monitor, comparing the dispensing detected with information concerning the desired dosing regimen for the certain medication and displaying graphically to the patient at least one feedback indication of the patient's degree of compliance or deviation with the desired regimen.

22 Claims, 4 Drawing Sheets

MEDICATION CONTAINER AND DOSING MONITOR

RELATED APPLICATIONS

This application is a continuation of Ser. No. 11/941,796, filed Nov. 16, 2007, pending, which in turn, is related to and claims priority under 35 U.S.C. 119(e) of provisional patent application Ser. No. 60/859,806, filed Nov. 17, 2006, the both of which are incorporated herein by reference.

FIELD OF THE INVENTION

This invention is in the fields of medication event monitoring and monitors for use therein. More particularly this invention relates to a medication container which is capable of noting when doses of medication are dispensed from it and noting the degree of compliance of that medication dispensing to a defined medication regimen particularly defined by the pharmacodynamics of the specific medication being dispensed.

BACKGROUND OF THE INVENTION

It is well established that patient compliance with medication dosing regimens is a major factors in the effectiveness of the underlying medications. (As used herein, the term "compliance", when used in the context of a prescribed dosing regimen, is a neutral term which denotes not only the degree of conformance to the dosing regimen but also the degree of deviation from the dosing regimen. "Deviation", on the other hand, in this same setting is used to denote the degree of disparity noted between the observed dosing pattern and the prescribed regimen.) For a medication to achieve its potential benefit, the proper number of doses of the medication must be taken and the spacing between doses needs to be correct. There are literally thousands of medical and scientific journal reports which describe the negative consequences of patient failures to properly adhere to prescribed dosing regimens. In some cases these consequences are relatively benign but in other cases compliance failures can actually cause the medication to do harm such as when antivirals and antibacterials are taken in a haphazard manner and the patient is not cured but instead medication-resistant strains emerge and increase the severity of the patient's infection.

It is understood in the pharmaceutical arts that recording the times at which medication doses are taken and analyzing the information so gathered can have two beneficial effects. It can give the health care professional a record of whether or not the doses of medication are being taken as prescribed. In addition, the presence of a record causes the patients to actually be more compliant with their prescribed medication regimens.

Aardex Ltd, and its associated company, Aprex Corporation, have for several years marketed medication containers having caps and other closures which monitor the removal of medication doses by ambulatory patients and create a record of the medication dosing events. Patents which describe various aspects of these devices include U.S. Pat. Nos. 4,939,705, 4,725,997, 4,971,221, 6,822,554 and 4,748,600.

While these monitors have proven to be reliable tools for enhancing patient compliance and maintaining a record of that compliance, it is now realized that monitoring devices with greater ability to adopt to a variety of different medications with differing pharmacodynamic properties would be advantageous. These differing pharmacodynamic properties among different drugs manifest themselves in differing degrees of sensitivity to deviations from prescribed regimens. Some drugs are relatively forgiving and exhibit only minor drop offs in effectiveness when the prescribed dosing pattern is poorly followed. Others have pharmacodynamic profiles which present major drop offs in effectiveness at the same degree of dosing deviation.

In addition, it has been taught that providing a monitor with the capability of communicating to the patient information about the prescribed dosing schedule and/or the patient's compliance to it can be beneficial in promoting compliance. However, it has been found that certain monitor-to-patient communications provide greater enhancements in compliance than others. It is desired to incorporate the ability to carry out such preferred communications into an improved monitor.

SUMMARY OF THE INVENTION

It has now been found that it is an improvement to a medication monitor capable of noting the time of dispensing of doses of medication, to equip such a monitor with pharmacodynamic information concerning the desired dosing pattern for the specific medication that the monitor is being used with such that the monitor can compare the times that it has noted with the dosing times called for by the desired dosing pattern. As used herein, "pharmacodynamic data", "pharmacodynamic information" and like terms refer to drug-specific information on the effects of the drug on typical patients as a function of drug concentration and on changes in drug concentration in a typical patient over time after dosing. In particular, this pharmacodynamic information can include information on the relative effectiveness of the particular drug at various levels of deviation in dosing times from the desired or prescribed dosing schedule.

With this improvement the monitor includes a processor (also referred to as a "comparator") capable of comparing the time elapsed since at least the most recently-generated "dose-dispensed" time and/or the time between the most recently-generated "dose dispensed" time noted by the monitor and at least one previous dose-dispensed time noted by the monitor with the pharmacodynamic information concerning the desired dosing regimen for the specific medication.

The monitor generates one or more outputs indicative of the degree of compliance between the period of time elapsed since at least the most recently-generated dose-dispensed time and/or the time elapsed between the most recently-generated dose-dispensed time signal and said at least one previous dose-dispensed time signal. This output takes into account the pharmacodynamic information concerning the desired dosing regimen for the certain medication and is an indication of the pharmacodynamic effects of the degree of deviation from the prescribed regimen. Preferably, this output is a graphic output such as a visible color change, a pie chart, a bar chart or the like. Also preferably, this output can be an indication of the potential severity of the detected deviation.

In accord with this invention, improvements have now been found to medication monitors capable of noting and preferably also recording the time of dispensing of doses of medication to patients. This improvement is to equip such a monitor with pharmacodynamic information concerning the desired dosing pattern for the specific medication that the monitor is being used with. This pharmacodynamic information includes information on the effects of various deviations from this desired dosing pattern. With this improvement the monitor is additionally equipped to compare the times that it has noted with the dosing times called for by the desired dosing pattern, and providing to the patient an indication of the degree of compliance with and/or deviation from the desired dosing pattern and/or the severity of the effect resulting from the observed degree of compliance or deviation based upon the pharmacodynamic information.

Thus, in one embodiment this invention provides a patient-portable medication event monitor which includes the following components:

A container capable of housing a plurality of doses of a certain medication. This container includes a detector capable of detecting the dispensing of these doses of this medication from the monitor;

A clock for generating a dose-dispensed time signal each time a dose of this medication is dispensed from the monitor;

A time signal memory for storing the dose-dispensed time signals generated by the clock;

A dosing regimen memory for storing pharmacodynamic information concerning the desired dosing regimen for the certain medication and the effects of various deviations from the desired dosing regimen;

A comparator for comparing the time since at least the most recently-generated dose-dispensed signal or the time between the most recently-generated dose-dispensed time signal and at least one previous dose-dispensed time signal noted by the monitor with the pharmacodynamic information concerning the desired dosing regimen for the certain medication. This comparator generates an output indicative of the current degree of compliance since at least the most recent dose-dispensed time signal or between the most recently-generated dose-dispensed time signal and at least one previous dose-dispensed time signal and the pharmacodynamic information concerning the desired dosing regimen for the certain medication. In certain embodiments the comparator can generate an output indicative of the severity of the effect resulting from the observed degree of compliance or deviation based upon the pharmacodynamic information; and A display for displaying to the patient a graphic indication of the output of the degree of compliance or deviation or the severity of the effect resulting from the observed degree of deviation based upon the pharmacodynamic information.

In additional, more specialized embodiments this monitor can include a clock for generating a current daily time period and a display for displaying to the patient the number of doses of the certain medication dispensed from the container during the then current daily time period.

Additionally this monitor can include a display for displaying to the patient the time since the last dispensing of a dose.

The medication monitors of the invention store the dose-dispensed times in memory contained within the medication monitor. This information can be down-loaded to a computer and outputted to a healthcare professional or service. This outputting can take place by connecting to the monitor with a plug or it can be done in a contactless manner using optical or infrared coupling, ultrasonic coupling, capacitance coupling, inductive coupling, radio or telephone coupling, such as for example "Bluetooth" radio coupling or the like.

In one popular embodiment the monitor is located within a container closure such as a pill bottle cap which is opened to dispense each dose of the medication from the container and wherein the opening (or opening and closing) of the closure generates a signal which is detected and upon which a "dose-dispensed" indication of the dispensing of the medication is based.

In another popular embodiment the monitor is associated with a blister pack containing unit dosage forms of the medication and the dispensing of a dosage form out of the blister pack generates the signal which is detected and upon which the "dose-dispensed" indication of the dispensing of the medication is based.

In yet another embodiment this invention provides the processes of monitoring patient compliance with medication regimens which are carried out when the above-described monitors are employed.

DETAILED DESCRIPTION OF THE INVENTION

Brief Description of the Drawings

This invention will be further described with reference being made to the accompanying drawings. In these drawings.

DESCRIPTION OF THE EMBODIMENTS

Figure 1:
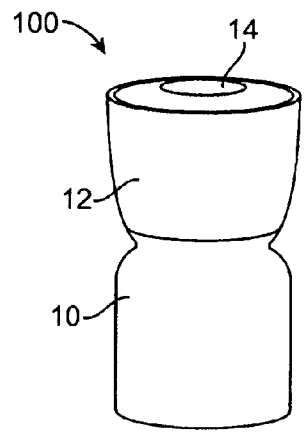
FIG. 1 is a perspective view of a medication dosing event monitor embodied as a pill bottle with a removable cap in which the electronics for monitoring and storing data concerning medication events and pharmacodynamic information are housed and in which a display for communicating information to the patient concerning the patient's compliance with the medication regimen is also provided.
Figure 3:
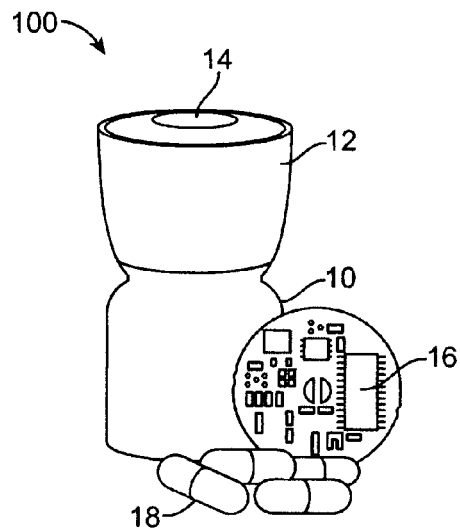
FIG. 3 is a cut away view depicting schematically the electronics housed in the cap.
Figure 2:
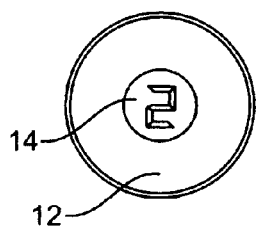
FIG. 2 is a top view of the monitor shown in FIG. 1.

The monitors of this invention take the form of a medication dose container equipped with electronics for providing the monitoring functions. As shown in FIGS. 1, 2, and 3 the monitor can take the form of a pill bottle 100 having a body 10 and a removable cap 12. Cap 12 includes a patient-readable display which provides information to the patient concerning the patient's level of compliance with the prescribed dosing pattern for the medication. When the cap 12 is opened (or when the cap is opened and closed) a signal is generated corresponding to that opening (or opening and closing) which the monitor uses as an indication that a dose of medication, such as one or more pills 18, has been removed from the pill bottle 10 and taken by the patient. This defines a dosing event. This signal is passed to circuit board 16 which contains a processor which includes a power supply, clock and memory. The processor in circuit board 16 generates one or more patient-detectable feedback signals which are most often visual signals that are set out to the patient on display 14. As will be described in more detail below these feedback signals can provide direct information to the patient, such as the number of dosing events detected that day and/or the length of time since the last dosing event or the length of time until the next dosing event.

The feedback signal will also be/or include one or more indirect signals calculated by the processor based upon the detected dosing times and pharmacodynamic data stored in the memory. In particular, an indirect feedback signal can be generated by comparing the time since at least the most recently detected dosing event and/or the time or times elapsed between the most recently detected dosing event and one or more prior dosing events with the desired dosing times which have been prescribed and which are stored in the memory. This comparison provides deviation data between the desired dosing times and the detected dosing times. This deviation data is compared with pharmacodynamic data concerning the medication being dispensed which are also stored in the memory. This pharmacodynamic data expresses the severity of the effect of various deviations on the patient's well-being and leads to one or more signals to the patient indicating or reflecting this severity based upon the measured deviations in the measured dose times and the stored pharmacodynamic information.

When describing the times or the periods of time which are used with the pharmacodynamic information to determine the severity of the patient's deviation from the prescribed regimen, reference is often made to the use of "at least" a particular time or period. This is done to assure that it is understood that when determining the pharmacodynamic effects of deviations from dosing schedules the more data points collected or the longer the period over which the data points are collected the more definite and reliable the determinations are. Thus, a pharmacodynamic deviation determination based on only the time elapsed since a most recent dosing event or a period of time elapsed between say the most recent two detected dosing events is likely be less reliable than similar determinations using more time period data.

Figure 4:
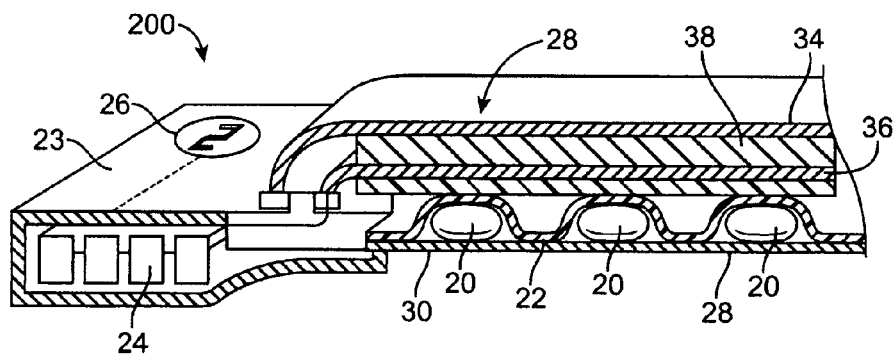
FIG. 4 is a partially schematic, partially cross-sectional perspective view of a medication dosing event monitor embodied as a blister pack in a blister pack holder in which the electronics for monitoring and storing data concerning medication events and pharmacodynamic information concerning the medication are housed. This monitor includes a display for communicating information to the patient concerning the patient's compliance with the medication regimen.

The pill bottle 100 shown and just described is merely representative. The medication dispenser could take the form of any medication dispenser, such as a blister pack, an inhaler, a nebulizer, a blister pack or the like. An example of these other forms is blister pack 200 shown in FIG. 4. In blister pack 200 doses of medication 20 are in a blister 22. Blister 22 is placed in holder 23 which additionally contains the circuitry 24 and display 26 which enable the device to detect dosing events, create a record of these events and provide output to the patient concerning the patient's compliance with the dosing regimen for the medication. Pack 22 could contain a series of electrical traces which are disrupted when a dose 20 of medication is ejected downward through layer 28. This disruption of electrical traces provides a signal that a dose of medication 20 has been dispensed and that dose-dispensed signal could be used as described with reference to pill bottle 100.

Alternatively, as shown, the electrical signal indicative of dispensing of a medication dose form can be generated by applying pressure at a point 28 adjacent to a dose of medication 20. This pressure would, in addition to pressing dose 20 out of blister 22 through layer 30 disrupt the relationship between conductive layers 34 and 36, separated by separation layer 38 and thereby generate a change in the electrical signature of the layers 34, 36 and 38. This change in electrical signature can be detected by circuit 24 located in blister holder 23 as an indication that a dose of medication has been dispensed and can serve as a dose-dispensed signal.

This dose-dispensed signal can be associated with a time signal generated by the clock in the monitoring circuit 24 and this time information concerning the dose taking can be stored in memory. This time signal and its relation to other previous dose-detected signals and/or its relationship to the time elapsed at least since its detection can also be analyzed with the specifically-entered pharmacodynamic dosing effect information to determine the patient's degree of compliance with the specific prescribed dosing regimen for this particular medication. This analysis yields a indication of the severity of the effects on the patient caused by the deviations from the regimen. The results of this analysis can be stored in the memory as well.

The comparison of the observed time either since at least the most recent dose-dispensed time or between the most recent dose-dispensed time and least one additional prior dose-dispensed time stored in the memory are used to generate a feedback signal which is conveyed to the patient. This feedback signal is based on the pharmacodynamic information and algorithm loaded into the monitor. This information is drawn up specifically for the precise medication being dispensed and is based upon the pharmacodynamics of this exact medication. This information and algorithm take into account the duration of action and rate of clearance of the particular medication being dispensed.

The feedback signal is based upon the time since at least the most recent dose-dispensed time and/or at least the time between the most recent dose-dispensed time and at least one previous dose-dispensed time. It can also be based upon the most recent dose-dispensed time and at least two additional prior dose-dispensed times and more preferably the most recent time and at least three prior dose-dispensed times. The function of this feedback signal is to give the patient an indication of the patient's overall level of compliance, or described conversely, an indication of the severity of the patient's deviations from the desired dosing pattern for the specific medication.

This overall compliance feedback signal can be based upon the most recent dose dispense time and the time elapsed since it was noted. However, it generally will be based upon historic dosing times to some extent, so as to give a relatively long range view of the patient's degree of compliance, such as over a rolling several day period (say of up to about five days, i.e. 120 hours). The compliance feedback signal will, however, be weighted in favor of the patient's observed degree of compliance over the more recent portion of that period such as over the most recent 12 to 48 hours. In all cases the compliance feedback signal given will be based upon a comparison of the observed dosing pattern with the particular algorithm and pharmacodynamic information in the memory which are in turn based upon the pharmacodynamic properties of the particular medication being dispensed.

The compliance feedback signal is provided to alert the patient if there has been a dosing error in this more recent period and also to inform the patient about the severity of the error and/or the patient's overall adherence to the prescribed regimen. It can also provide similar information concerning the wider time period.

In addition to determining and providing this overall compliance feedback signal, the medication monitor can, if desired, provide additional information to the patient concerning the patient's current dosing activities. This additional information can include an indication of the number of container openings or openings and closings (and hence dosings) detected during the current day. To provide this information the medication monitor is equipped with a clock that can provide a daily start time and also provide a suitable day interval, most typically a 24 hour interval beginning with the start time. Based upon this start time and the subsequent 24 hour or other day interval and noting the number of dosings occurring within that interval, the "daily doses taken" number can be generated and displayed to the patient.

Another piece of information that the monitor can calculate and display to the patient is the length of time that has elapsed since the patient's most recent dose. This "time since last dose" period can run continuously from day to day or alternatively can zero itself at a preset time each day, such as the beginning of the 24 hour period noted above for determining daily dose levels. It can also rezero the period at that time and only restart the calculation of this value when the patient takes a first dose at the beginning of the next day.

It is generally preferred to provide the compliance feedback signal in a graphic form rather than in an alphanumeric manner. If the number of doses taken in the current day is being displayed to the patient this is generally provided numerically. The time since last dose can be provided numerically as well but more commonly is provided in a graphic form.

Figure 5:
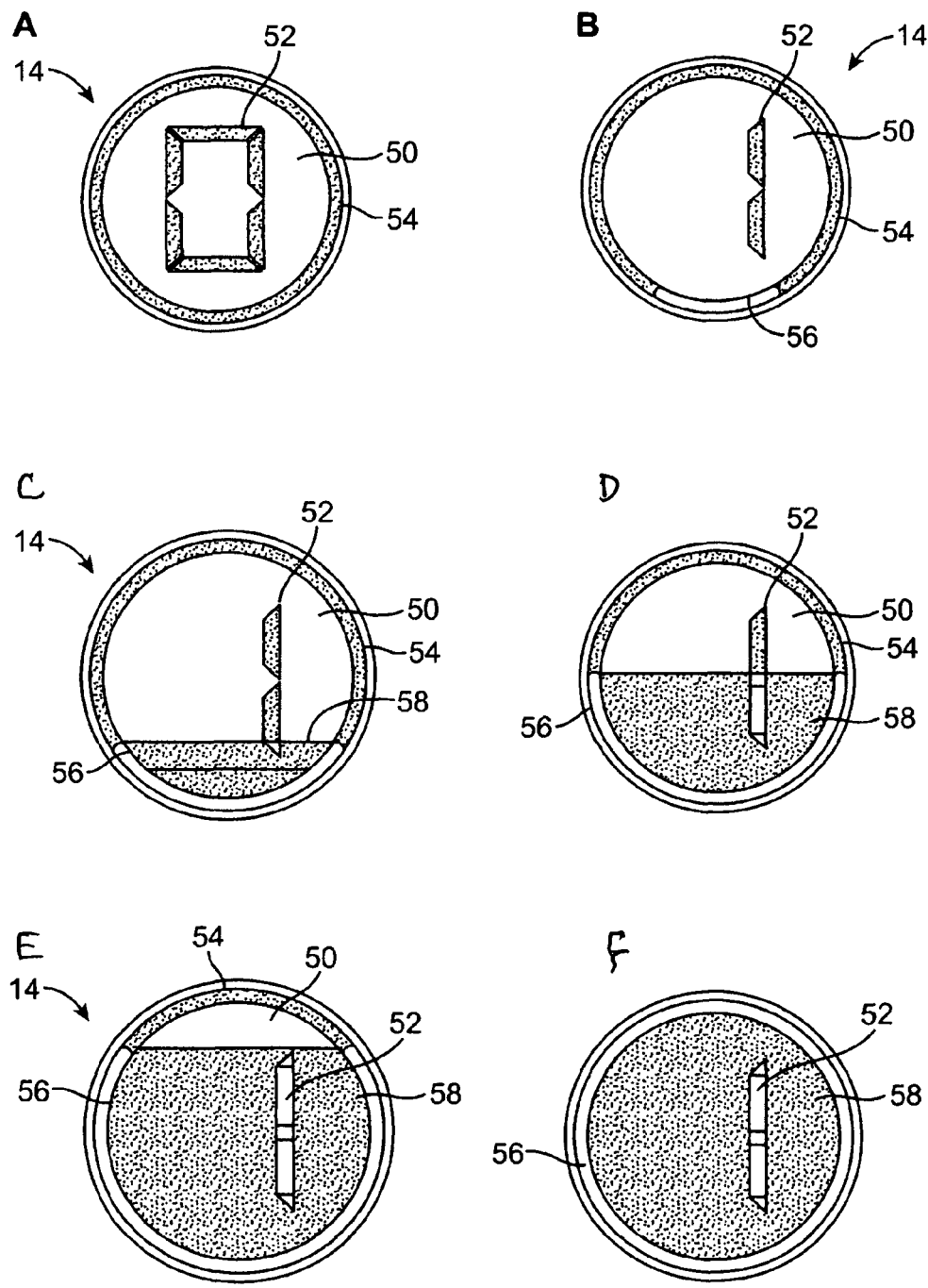
FIG. 5 is a diagrammatic depiction of a display useful in the monitors of the invention for depicting graphically to the patient the patient's level of compliance. This figure includes ten separate views showing display outputs relating to the patient's degree of compliance with a medication regimen.
Figure 5:
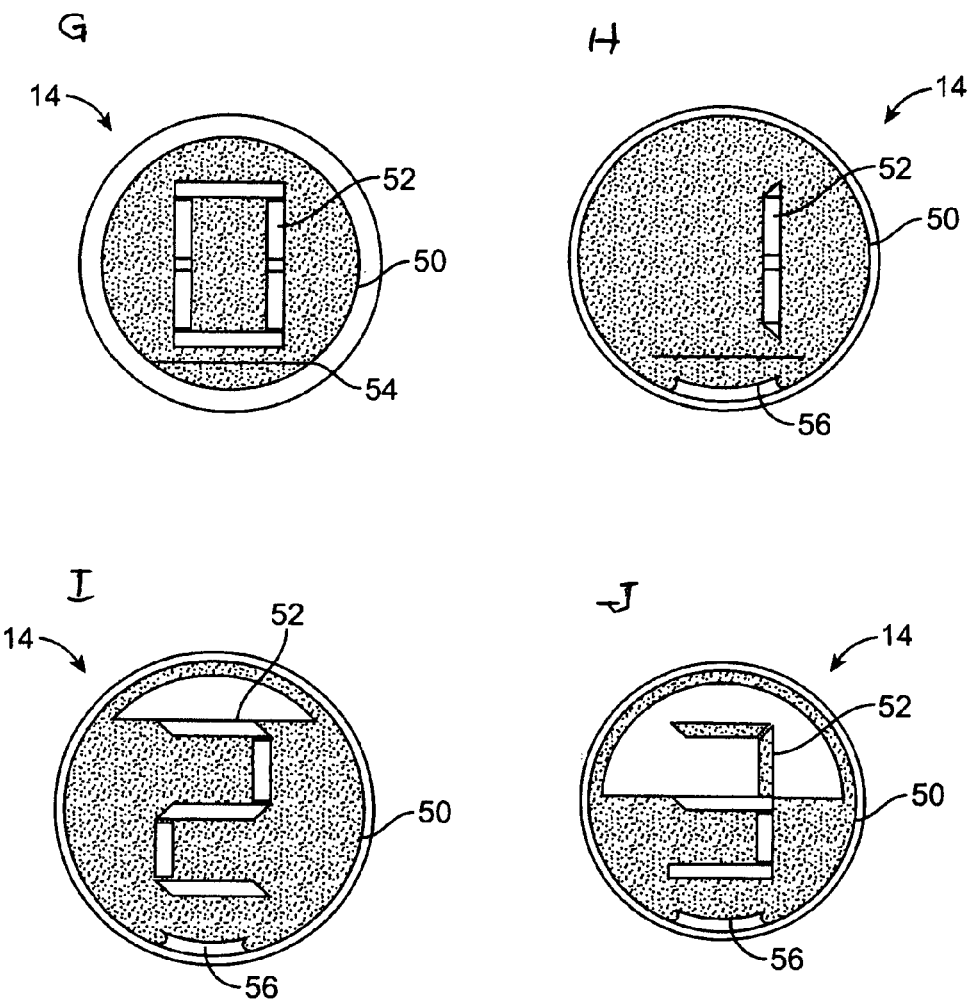
Figure 6:
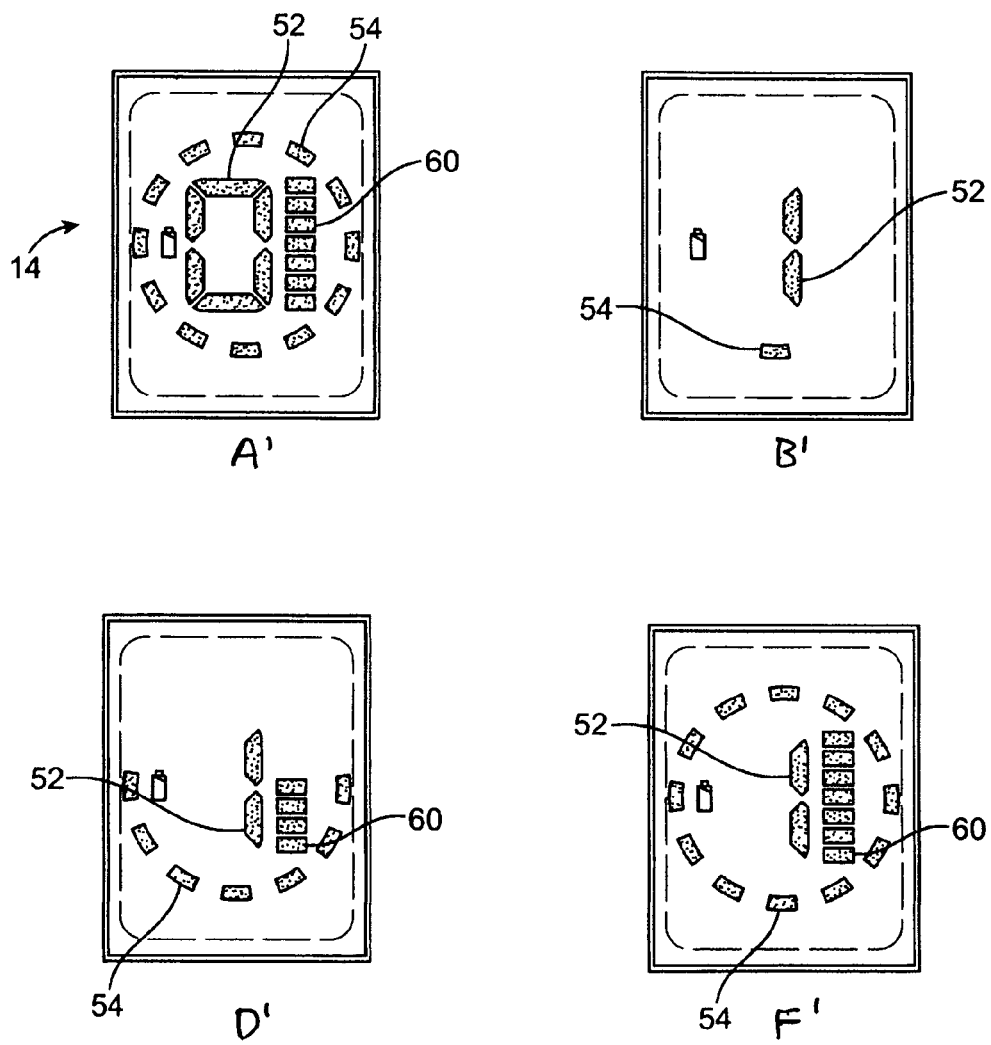
FIG. 6 is a diagrammatic depiction of an alternative display useful in the monitors of the invention for depicting graphically to the patient the patient's level of medication compliance. Four separate display views are presented.

FIGS. 5 and 6 depict two representative display formats for the compliance feedback signal. Display formats for the optional "daily doses taken" signal and the "time sine last dose" signal are shown as well.

In FIG. 5, the compliance feedback signal is provided in the form of a graduated color change in the background 50 of display 14. Numeric character 52, ("0" and "1" in FIG. 5) representing the number of doses taken during the day is displayed in the center of the display. A graduated segmented band 54 encircling the edge of the display graphically displays the time since last dose in the form of a change of color of segments of the band with larger numbers or longer lengths of segments being changed to represent longer periods since last dose and smaller numbers or shorter lengths of changed segments representing shorter intervals since the most recent dose.

FIG. 5 shows ten views of the display 14 depicted on A through J respectively. View A shows the display 14 before it is activated. It includes a background 50, an alphanumeric display 52 and a surrounding contrasting color segmented band 54. (For the purposes of this explanation it is postulated that the medication being delivered is one which is supposed to be taken three times a day with six hour spacing between successive doses.) View B represents the display after a first dose has been taken and before a second dose should be taken to conform to the algorithm specially programmed into the processor of the monitor. In View B the alphanumeric display 52 is showing that the monitor has detected "1" dose taken on this particular day. A small segment 56 of segmented band 54 has changed color to indicate that a period of time of about four or five hours has elapsed since the last does. (This is based on a "24 hour clock" display where the full circle of display 54 represents 24 hours and the segment 56 represents about a fifth or a sixth of the complete circle, hence four to five hours. Because this 4 to 5 hour time period since the last dose is well within the dosing schedule for this particular medication which has been programmed into the detector, the "overall compliance feedback signal" presented by the background color is indicates that everything is on schedule and that no therapeutic error has occurred.

View C shows the display that would result if eight hours had passed and the second dose of medication had not been taken. This deviation with this particular drug would be considered a minor deviation. Display 52 shows that only one dose has been taken for this particular day. The "changed color" portion 56 of the surrounding band has expanded to represent about one third of the 24 hour day since last dose, or eight hours. A portion 58 of the background is displayed in a changed color to indicate the a dose is overdue and that a minor therapeutic error has occurred and been detected and a changed "compliance feedback signal" is being displayed.

View D shows the same display after a twelve hour period has elapsed without the second dose of medication being taken. The alphanumeric display 52 still shows that one dose has been taken this day, The surrounding band 54 now shows that one half of the 24 hour period it represents (twelve hours) has changed color to 56 to represent that twelve hours has passed since the last dosing. Now a larger portion 58 of the background 50 has changed color to indicate that that therapeutic error has grown in severity and hence this more negative compliance feedback signal is being provided.

Views E and F illustrate how the display would change if the second dose was still not taken after, say, 16 hours and after 24 hours. Larger and larger regions of the surrounding band 54 and the background area 50 would change color to reflect the longer and longer periods of error and the increasing severity of the error with this particular drug to "severe" (E) or "catastrophic" (F) and an increasingly negative compliance feedback signal.

This description of these first six views of FIG. 5 has shown a relatively linear correspondence between the period of dosing error and severity of the dosing error reflected in the compliance feedback signal. As has been noted, the algorithm which controls this display is specially tailored for the specific medication being administered. The severity of error indication provided by the background change indicative of the compliance feedback signal need not move linearly with time if the pharmacodynamics of the medication dictate otherwise.

In addition to being used to control the information depicted on display 14, the dosing history generated by the monitor is placed in memory for eventual communication to the patient's healthcare professional or to an intermediate service supplying patient compliance information to the healthcare professional supervising the patient's treatment. This information about the errors which were detected in the patient's dosing of the medication can also play a part in determining the next day's compliance feedback signals as shown in views G, H, I and J. These four views provide a series of representative indications which might be displayed by display 14 on the day following the day in which the dosing history if views A through F was compiled.

View G shows the display on the second day before any dosing is detected, The alphanumeric display 52 and the outer band 54 have been reset by the processor to indicate that "0" doses have been taken on the second day and that no time period is running since the last dose. The background 50 is still displaying a completely changed color indicative of the catastrophic therapeutic error which occurred the previous day.

View H shows the display on the second day after a first dosing that day is detected, The alphanumeric display 52 shows that "1" dose has been dispensed. The outer band 54 indicates that an acceptable time period is running since that first dose. However, the background 50 is still displaying a completely changed color indicative of a compliance feedback signal reflecting the catastrophic therapeutic error which occurred the previous day.

Views I and J show the display on the second day after a second and a third dosing that day are detected, The alphanumeric display 52 shows that "2" and "3" doses have been dispensed during the second day. The outer band 54/56 indicates that an acceptable time period is running since the last of these doses. The background 50 is still displaying a partially changed color indicative of an overall compliance feedback signal based in part upon the therapeutic error which occurred the previous day but which is being gradually corrected for by the proper dosing on this second day.

It will be appreciated that since the algorithm and pharmacodynamic information are tailored specifically to the medication being dispensed, these changes in the compliance feedback signal (or lack thereof) can be specifically programmed. In some cases an error as severe as detected on the first day might not be corrected by proper dosing on the next day and the only acceptable outcome of the monitoring is for the patient to contact the health care professional or service. In other cases, as shown, the subsequent proper dosing may be able to make up for the earlier error.

An alternative display protocol is depicted in FIG. 6 as views A'. In this embodiment a display 14 is provided which includes the alphanumeric display 52 of the number of doses taken and a circumferential display 54 of the length of time since the last dose. The display 14 includes a bar graph display 60 depicting the compliance feedback signal with a larger number of bars in this display indicating increasing severity of a detected error. View A' corresponds to view A, as just described in FIG. 5. View B' corresponds to view B in FIG. 5. View D' corresponds to view D in FIG. 5. View F' corresponds to view F in FIG. 5.

In all of the embodiments just described the compliance signal is provided as a segmented change in color of a figure, or a background. To the extent that these changes are depicted as light or dark in color this is merely representative. Colors could be changed or reversed as desired to give the most appealing or informative display.

The monitors of this invention, in addition to providing a series of signals to the patient alerting the patient to various factors relating to the patient's compliance with the desired regimen store a record of the patients medication dosing activates. This record can be read out periodically to the patient's health care professional. This read out can be carried out by connecting the monitor to a communication device or it can be carried out via a contactless connection as set forth in U.S. Pat. No. 5,917,429, which is incorporated herein by reference.

We claim as our invention:

1. A method for monitoring the compliance between the timing of medication events for a certain medication and for providing feedback indicative of the degree of compliance between those monitored medication events and a specified dosing regimen, where both the specified dosing regimen and the degree of compliance are determined using pharmacodynamic information including at least dosing effect information for the certain medication and information on the effects of various deviations from the specified dosing regimen, wherein the degree of compliance is provided at least to a patient receiving such medication comprising the steps of:
   a.) providing to a dosing regimen memory and storing therein pharmacodynamic information for the certain medication comprising a desired dosing regimen, dosing effect information, and information on the effects of various deviations from the specified dosing regimen,
   b.) monitoring the time that a dose of said medication is taken by the patient to provide a dose time signal,
   c.) providing the dose time signals to a time signal memory for storage,
   d.) determining at least the time elapsed since the most recently-generated dose time signal or the time elapsed between the most recently generated dose time signal and at least one previous dose time signal,
   e.) comparing such determined elapsed times with the pharmacodynamic information concerning the dosing regimen, dosing effect information for the certain medication, and information on the effects of various deviations from the specified dosing regimen,
   f) generating a feedback output indicative of the degree of compliance between the determined times and the pharmacodynamic information concerning the desired dosing regimen, dosing effect information, and deviation effect information for the certain medication, and
   g.) displaying to the patient a graphic indication of the feedback output of the degree of compliance.

2. The method of claim 1 wherein the step of determining at least the time elapsed since the most recently-generated dose time signal or the time elapsed between the most recently generated dose time signal and at least one previous dose time signal comprises a step selected from:
   a.) the step of determining at least the time between the most recently generated dose time signal and at least one previous dose time signal,
   b.) the step of determining at least the time between the most recently generated dose-detected time and the next most recently generated dose detected time, and
   c.) the step of determining at least the time between the most recently generated dose time and the next most recently generated dose detected time and the time between at least another pair of dose detected times.

3. The method of claim 1 additionally comprising the step of providing data concerning the patient's dosing history with the certain medication to a health care professional or service.

4. The method of claim 1 wherein the step of displaying to the patient a graphic indication of the feedback output comprises displaying the degree of compliance as a bar graph, a pie chart, or a visible color change.

5. The method of claim 4 wherein the graphic indication of feedback comprises a visible color change display and the visible color change display indicates a potential severity of the patient's deviations from a desired dosing pattern of the certain medication.

6. The method of claim 1 wherein the step of monitoring the time that a dose of said medication is taken by the patient comprises monitoring the time that a dose of the certain medication is removed from a blister pack.

7. A device for monitoring the compliance between the timing of medication events for a certain medication and for providing feedback indicative of the degree of compliance between those monitored medication events and a specified dosing regimen, where the specified dosing regimen and the degree of compliance are determined using pharmacodynamic information including at least dosing effect information for the certain medication and information on the effects of various deviations from the specified dosing regimen, wherein the degree of compliance is provided at least to a patient receiving such medication comprising:
   a.) a medication timing detector capable of providing a dose time signal to a time signal memory each time a dose of said medication is taken by the patient,
   b.) the time signal memory for storing the dose time signals provided by the medication timing detector,
   c.) dosing regimen memory for storing pharmacodynamic information concerning the desired dosing regimen, dosing effect information, and deviation effect information for the certain medication,
   d.) a comparator for determining at least the time elapsed since the most recently-generated dose time signal or the time elapsed between the most recently generated dose time signal and at least one previous dose time signal and comparing such determined elapsed times with the pharmacodynamic information concerning the dosing regimen, dosing effect information, and deviation effect information for the certain medication and generating a feedback output indicative of the degree of compliance between the determined times and the pharmacodynamic information concerning the desired dosing regimen, dosing effect information, and deviation effect information for the certain medication, and e.) a display for displaying to the patient a graphic indication of the feedback output of the degree of compliance.

8. The device of claim 7 wherein the comparator is operative to determine at least the time between the most recently generated dose time signal and at least one previous dose time signal and comparing such determined times with the pharmacodynamic information concerning the dosing regimen, dosing effect information, and deviation effect information for the certain medication and generating a feedback output indicative of the degree of compliance between the determined times and the pharmacodynamic information concerning the desired dosing regimen and dosing effect information for the certain medication.

9. The device of claim 8 wherein the at least the time between the most recently-generated dose-dispensed time signal determined time and at least one previous dose-dispensed time signal is the time between the most recently generated dose-detected time and the next most recently generated dose detected time.

10. The device of claim 8 wherein the at least the time between the most recently-generated dose time signal determined time and at least one previous dose time signal is the time between the most recently generated dose time and the next most recently generated dose detected time and the time between at least another pair of dose detected times.

11. The device of claim 7 additionally comprising a dispensing data output by which data concerning the patient's dosing history with the certain medication can be outputted to a health care professional or service.

12. The device of claim 11 wherein the dispensing data output is a contactless communication connection by which data is outputted by a connection selected from optical connections, capacitance connections, inductive connections, radio connections, and telephone connections.

13. The device of claim 7 wherein the display for displaying to the patient a graphic indication of the feedback output displays the degree of compliance as a bar graph, a pie chart, or a visible color change.

14. The device of claim 7 wherein the graphic indication of the feedback output displays the degree of compliance as a visible color change and the visible color change display indicates a potential severity of the patient's deviations from a desired dosing pattern of the certain medication.

15. A blister pack device for housing a plurality of doses of a certain medication and for monitoring the compliance between the timing of medication events for the certain medication and for providing feedback indicative of the degree of compliance between those monitored medication events and a specified dosing regimen, where the specified dosing regimen and the degree of compliance are determined using pharmacodynamic information including at least dosing effect information for the certain medication and information on the effects of various deviations from the specified dosing regimen, wherein the degree of compliance is provided at least to a patient receiving such medication comprising:

a.) a blister pack container capable of housing a plurality of doses of the certain medication, b.) a medication timing detector capable of providing a dose time signal to a time signal memory each time a dose of said medication is taken by the patient, c.) the time signal memory for storing the dose time signals provided by the medication timing detector, d.) dosing regimen memory for storing pharmacodynamic information concerning the desired dosing regimen, dosing effect information, and deviation effect information for the certain medication, e.) a comparator for determining at least the time elapsed since the most recently-generated dose time signal or the time elapsed between the most recently generated dose time signal and at least one previous dose time signal and comparing such determined elapsed times with the pharmacodynamic information concerning the dosing regimen, dosing effect information, and deviation effect information for the certain medication and generating a feedback output indicative of the degree of compliance between the determined times and the pharmacodynamic information concerning the desired dosing regimen, dosing effect information, and deviation effect information for the certain medication, and f.) a display for displaying to the patient a graphic indication of the feedback output of the degree of compliance.

16. The device of claim 15 wherein the comparator is operative to determine at least the time between the most recently generated dose time signal and at least one previous dose time signal and comparing such determined times with the pharmacodynamic information concerning the dosing regimen, dosing effect information, and deviation effect information for the certain medication and generating a feedback output indicative of the degree of compliance between the determined times and the pharmacodynamic information concerning the desired dosing regimen and dosing effect information for the certain medication.

17. The device of claim 16 wherein the at least the time between the most recently-generated dose-dispensed time signal determined time and at least one previous dose-dispensed time signal is the time between the most recently generated dose-detected time and the next most recently generated dose detected time.

18. The device of claim 16 wherein the at least the time between the most recently-generated dose time signal determined time and at least one previous dose time signal is the time between the most recently generated dose time and the next most recently generated dose detected time and the time between at least another pair of dose detected times.

19. The device of claim 15 additionally comprising a dispensing data output by which data concerning the patient's dosing history with the certain medication can be outputted to a health care professional or service.

20. The device of claim 19 wherein the data output is a contactless communication connection by which data is outputted by a connection selected from optical connections, capacitance connections, inductive connections, radio connections, and telephone connections.

21. The device of claim 15 wherein the display for displaying to the patient a graphic indication of the feedback output displays the degree of compliance as a bar graph, a pie chart, or a visible color change.

22. The device of claim 21 wherein the graphic indication of the feedback output displays the degree of compliance as a visible color change and the visible color change display indicates a potential severity of the patient's deviations from a desired dosing pattern of the certain medication.

* * * * *